United States Patent [19]
Raimondo

[11] Patent Number: 5,919,180
[45] Date of Patent: *Jul. 6, 1999

[54] PAD ASSEMBLY FOR ABSORBING FLUIDS

[76] Inventor: Rick Raimondo, 5A Brookdale Gardens, Bloomfield, N.J. 07003

[ * ] Notice: This patent issued on a continued prosecution application filed under 37 CFR 1.53(d), and is subject to the twenty year patent term provisions of 35 U.S.C. 154(a)(2).

[21] Appl. No.: 08/692,415

[22] Filed: Aug. 5, 1996

[51] Int. Cl.$^6$ .............................. A61F 13/15; A61F 13/00; A61J 13/00; A41C 3/00
[52] U.S. Cl. .......................... 604/387; 604/389; 604/390; 604/385.1; 128/888; 128/890; 602/41; 602/42; 602/54; 450/37; 450/81
[58] Field of Search .................................. 602/41, 42, 43, 602/44, 47, 54, 55, 57, 58, 59, 903; 128/888–894; 119/852; 604/327, 346, 358, 385.1, 386, 387, 389, 390; 2/104; 450/30, 37, 54–57, 60–63, 81, 88

[56] References Cited

U.S. PATENT DOCUMENTS

| | | |
|---|---|---|
| 697,637 | 4/1902 | Lee ........................................... 128/888 |
| 1,094,158 | 4/1914 | Mattson . |
| 1,095,109 | 4/1914 | Harrington . |
| 1,165,275 | 12/1915 | Montgomery ............................ 128/890 |
| 2,452,345 | 10/1948 | Anselmo . |
| 2,476,869 | 7/1949 | Hughes ................................. 604/385.1 |
| 3,513,852 | 5/1970 | Seidl ......................................... 450/36 |
| 3,530,859 | 9/1970 | Heim ..................................... 604/385.1 |
| 4,324,237 | 4/1982 | Buttaravoli ................................. 602/54 |
| 4,787,381 | 11/1988 | Hubbard et al. ........................... 602/44 |
| 4,870,977 | 10/1989 | Imonti ..................................... 604/346 |
| 5,024,628 | 6/1991 | Sanchez ..................................... 450/36 |
| 5,086,763 | 2/1992 | Hathman ................................. 128/888 |
| 5,354,261 | 10/1994 | Clark et al. ............................. 128/888 |
| 5,449,340 | 9/1995 | Tollini ..................................... 128/888 |

FOREIGN PATENT DOCUMENTS

| | | | |
|---|---|---|---|
| 9230243 | 2/1993 | Australia ................................. 450/36 |
| 580420 | 8/1958 | Italy ......................................... 602/58 |
| 75767 | 9/1917 | Switzerland ............................. 450/36 |
| 2197590 | 5/1988 | United Kingdom .................... 602/58 |

*Primary Examiner*—John G. Weiss
*Assistant Examiner*—K. M. Reichle
*Attorney, Agent, or Firm*—Andrew Auerbach

[57] ABSTRACT

The invention developed is a nursing pad assembly suitable for absorbing lacteal fluid which is conformable to the human breast. It includes a conformable casing comprising a central area and a plurality of outwardly extending fingers, the central area possessing a pocket having a front opening and a rear opening; an absorbent padding material located in the pocket and capable of being removed through the front opening; and adhesively attaching the outwardly extending fingers to an area surrounding the nipple in such fashion that the nipple will contact the absorbent padding material through the rear opening. When the absorbent padding material is removed from the pocket, the nipple will be exposed through the front opening to enable nursing without requiring removal of the entire pad assembly.

16 Claims, 1 Drawing Sheet

PAD ASSEMBLY FOR ABSORBING FLUIDS

BACKGROUND OF THE INVENTION

The number of women breastfeeding nationally is rising substantially as a consequence of the previously unrecognized health benefits to the infant and the psychological impact on the mother. However, pregnant and nursing women often experience discharge of lacteal fluid from their breasts that can soil clothing or bed linens and lead to possible embarrassment. Nipples may also become sensitive and painfully irritated if not protected during this period.

A few products are patented to address the problem of lacteal fluid leakage. Rushton, U.S. Pat. No. 3,840,012 (1974), describes a circular reservoir for the collection of lacteal fluid. London, U.S. Pat. No. 2,891,544 (1951), and Fitzgerald, U.S. Pat. No. 2,896,623 (1959), claim breast pads which are designed to absorb lacteal fluid. These breast pads are discarded after use and can be expensive. A brassiere is necessary to support the pads, while nursing requires the removal of both the brassiere and padding material. A more recent development in this area is the nursing brassiere. Alternatively, the nursing brassiere has a flap which opens to allow for nursing and can also accommodate an absorbent pad. The major drawback of a nursing or conventional brassiere with an absorbent pad is that women must wear the undergarment throughout the day and night to prevent soiling of their clothes or bed sheets and avoid possible embarrassment. With constant use, the straps of a brassiere become extremely uncomfortable and are often described as annoying and constricting.

Several references describe bandages or dressings that can be used to absorb wound fluids. Hathman in U.S. Pat. No. 5,086,763 has a open central chamber in register with a wound wherein an absorbent material is removably placed so as to contact the wound. A flap is used to cover and retain the absorbent material. A similar construction is used by Tollini as described in U.S. Pat. No. 5,449,340 wherein a tab made of a hooked fabric is used to cover the central chamber. Buttarovoli in U.S. Pat. No. 4,324,237 utilizes a flap arrangement to allow for access to a wound with a cover strip releasably affixed over the flap to protect the wound. Lifschutz in UK Patent Application No. GB 2,197,590 describes a series of adhesive components covering the central open area in a bandage such that the cover adhesive strip can be removed for inspection of the wound. Most of the bandage and dressing inventions cited above use adhesive attachments, which are often near the site of the wound. The cited references also use a flap, tab, or cover strips to retain absorbent material used to absorb fluids.

None of the prior art utilize a pocket or double sided encasement to hold the absorbent material piece which would eliminate the need for flaps, tabs or cover strips used in these cited inventions. Greater accessibility to the breast nipple is possible without these external retaining flaps, tabs or cover strips.

Other related products with different intended functions have been developed. A bust pad containing a pocket that holds a removable, padding material is detailed by Brauer in U.S. Pat. No. 2,505,458 (1946). Though the bust pad is held in place by a brassiere, the product does not allow for nursing and is not intended to absorb fluid. Inonti in U.S. Pat. No. 4,754,750 (1988) describes an areola and nipple surgical wound protector. The product contains a sterile pad with a central cut out, a transparent cone shaped nipple protector member, and four spaced adhesive tape strips for securing the nipple protector member over the patient's breast. This particular product is not designed to absorb nipple secretions, must be entirely removed to gain access to the breast, and is not washable or reusable. In addition, there is no suggestion that the method of attachment employed can be extended to a nursing pad.

OBJECTS OF THE INVENTION

One object of this invention is to prevent the breasts from wetting and subsequently staining the clothing of nursing mothers. The pad assembly is designed to receive an absorbent pad and offers the same wetness protection as a conventional nursing brassiere. The unique design allows the product to remain in place while nursing an infant or simply changing an absorbent pad. The elasticity of the material used in the construction of the product prevents leaking while the woman changes positions (e.g. standing to lying down).

Another object of the invention is to provide a double-sided encasement or pocket design rather than using flaps, tabs or cover strips over a front opening to retain an absorbent padding material so nursing can be performed with greater accessibility to a nipple. Opposing slits are used to facilitate insertion and removal of the absorbent padding material. This design has an inner layer and an outer layer of fabric in the pocket that allows the fabric of the pocket to be in contact with a breast even upon nursing. There are no hooks, clips, fasteners or microhooks.

Another object of the invention is to preclude the need for any adhesive attachment near a nipple of a breast. The encasement or pocket design of the instant invention may have adhesive only at its perimeter to prevent the encasement or pocket design, and thus the absorbent padding material inside it, from displacing.

Another object of this invention is to develop a comfortable and non-restricting nursing pad. With prolonged use the shoulder straps of a conventional nursing brassiere become uncomfortable and constricting. The instant invention has no shoulder straps (shoulder-strapless), and therefore is not confining or restricting if worn throughout the day and night. It is extremely lightweight, soft, comfortable, and durable. In fact, no straps or bands are used to hold the assembly in place rather the assembly is secured adhesively in place.

Another object of this invention is to have this same assembly act as an effective bandage over the breast and more particularly as a surgical wound dressing for the areola and nipple area following radical mastectomy or breast reconstructive surgery.

Accordingly, it is the principal object of the present invention to provide a new and improved nursing pad assembly designed to prevent soiling of clothes or bed linens as a result of lactation without the use of straps to constrict the person wearing the device.

Another principal object of the invention is to provide women an alternative method to prevent nipple irritation from clothing when they prefer not to wear a conventional brassiere with straps.

A further principal object of the invention is to provide an undergarment which facilitates nursing due to the presence of front and rear openings in register with each other that allows the mother to breastfeed when the absorbent material is removed.

Another principal object of this invention is to provide an improved surgical wound protector and bandage for the areola, nipple area, and other proximate areas of the breast that absorbs fluid from the wound and maintains sterility while allowing for easy inspection of the area when the absorbent material is removed.

DETAILED DESCRIPTION OF THE PREFERRED EMBODIMENT

FIGS. 1–4 depict the shoulder strapless pad assembly which is generally designated as 11 according to one embodiment of the invention. The pad assembly is comprised of an outer casing 1 designed to receive an absorbent padding material 2 (shown removably positioned within), outwardly extending fingers in the form of spaced fabric strips 7 extending in a radial fashion from the casing, and attachment means 8 for adhering the strips to a breast. The pad assembly is composed of two layers of soft, smooth, elastic, lightweight, and washable fabric material such as a segmented polyurethane elastomer. A polyurethane elastomer such as that manufactured by E. I. DuPont Company under the trademark SPANDEX is one example of this fabric. The fabric is be comfortable, conforming, and durable. One possible fabric pattern has the perimeter sewn together to form a casing or pocket having a seam and resembles a formee cross with the fabric strips having generally decreasing width as a function of the distance from the central region followed by increasing width at the distal ends. This fabric strip shape allows for enhanced contouring to a breast or wound surface and to improve adhesive capabilities. The seam is on the inside of the pocket to prevent skin irritation and to enhance the casing's appearance.

Figure 1:
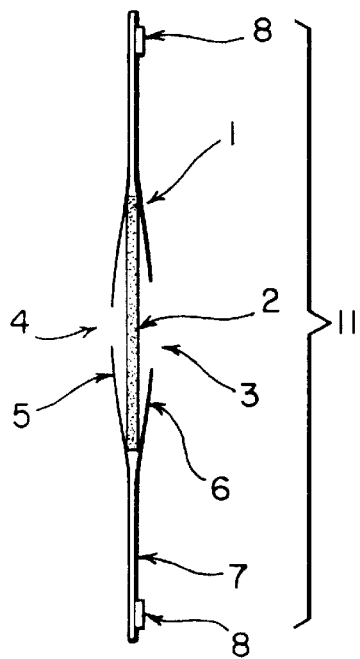
FIG. 1 is a side view of the pad assembly cross-section showing the casing and front and rear openings.
Figure 4:
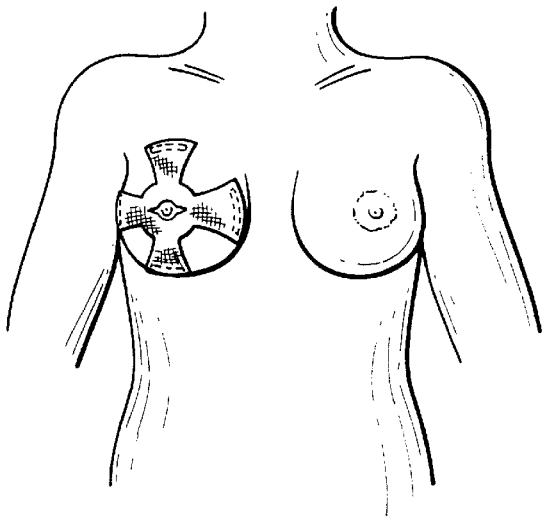
FIG. 4 is a perspective view of the pad assembly of the present invention on the breast.
Figure 2:
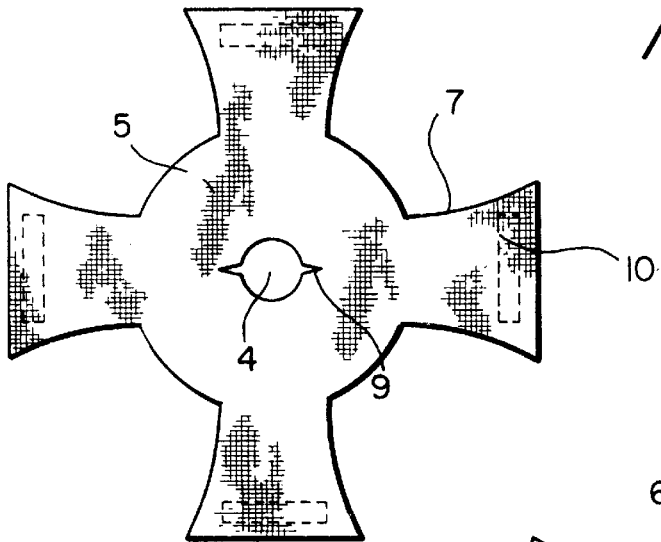
FIG. 2 is a top plan view of the front of the pad assembly.
Figure 3:
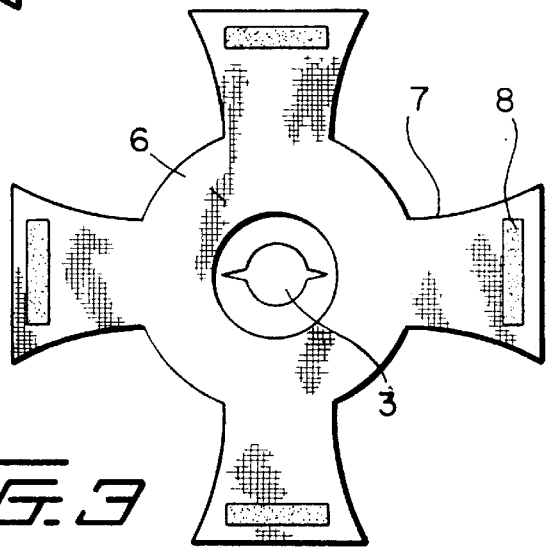
FIG. 3 is a top plan view of the rear of the pad assembly.

The front portion of the pad assembly, as illustrated in FIG. 2, contains a central circular area of fabric 5 with outwardly extending fingers in the form of four spaced fabric strips 7 extending radially out from the casing. One preferred embodiment has the fabric strips decreasing in width as a function of the distance from the central area of the fabric followed by increasing width at the distal ends. At the center of the casing 5 is a circular opening 4 optionally possessing slits 9 to facilitate removal of an absorbent padding material 2. In a preferred embodiment, the opening is one inch in diameter with the slits one half inch in length. The slits are on opposite sides of the opening, one hundred eighty degrees separated from one another, in the front of the casing and directed towards one of the spaced fabric strips. This configuration allows for easy insertion of an absorbent padding material, and at the same time prevents the pad from easily dislodging from the casing. The edges of the opening and slits are oversewn to avoid material fraying. The absorbent padding material is manufactured by several different companies (e.g. Evenflo Corporation, Inc.) and is constructed from multiple layers of cotton sheath, cotton flannel, or other high absorbency material. Nylon or polyester and cotton constructions are also known in the art. The absorbent padding material may be made of durable fibers, so that the material is washable and reusable. The padding material measures approximately three inches in diameter. The central casing may be embroidered for aesthetic and structural reasons.

The rear portion of the casing 6 contains a central circular area of fabric with four spaced fabric strips 7 extending radially out from the casing. At the center of the casing 6, is a circular opening 3 which in the preferred embodiment measures approximately two inches in diameter and is in register with the front opening 4. This design permits the nipple of a breast or the surgical wound to be in direct contact with the absorbent padding material. The edge of this hole 3 is oversewn to avoid material fraying. If the absorbent padding material is removed from the front opening 4, the nipple protrudes through both the rear and front openings to facilitate nursing. The double-sided encasement or pocket design has no flap, tap or cover strip to cover the front opening. This pocket design allows for good access to the nipple during nursing. If the instant invention is used as a surgical dressing on a breast, the wound would be available for inspection and cleaning after the absorbent pad is removed. A fresh absorbent pad 2 can be placed in the casing through the front opening 4 for continued absorbency of the lacteal fluid or wound drainage. Therefore, inserting and replacing an absorbent padding material can be performed without removing the pad assembly from its attachment to the skin. In one embodiment, the opening in the front of the casing will be greater than the opening in the rear of the casing to prevent the absorbent pad from dislodging. In another embodiment, the opening in the rear of the casing may be larger than the opening in the front to facilitate nursing or to facilitate inspection of a breast wound. In another embodiment of the pad assembly slits are created on opposite sides, one hundred eight degrees separated from one another, of the opening in front of the casing to allow for easy insertion of an absorbent padding material and to increase accessibility of the nipple to nursing.

The four fabric spaced strips 7 or arms of the cross-shaped product in the preferred embodiment measure three and one quarter inches in length from the center and are separated by a semicircular devoid area with a radius measuring one and one half inches. Therefore, the fabric strips or arms may flare out at the ends to improve adhesive capabilities. The front and rear fabric which form the four arms of the undergarment are sewn together at the distal ends to create a rectangular area 10 measuring one half inch by two inches. The perimeter of the fabric arms are also sewn together similar to the casing. By sewing the two sides of fabric together at their ends, the stability of the construct is improved, and the product subsequently adheres better to the skin. All edges of the pad assembly may be oversewn to prevent fabric fraying. Means for attachment, such as double sided adhesive tape 8, may be placed in the rectangular area on the rear surface.

In the preferred embodiment, the double sided adhesive tape is hypoallergenic and approved for human use. The tape adheres well to the pad assembly and to the skin. The skin must be clean, dry, and free of oil to insure effective adhesion. Other important qualities of the tape are its elasticity to stretch with the skin, and a micropore design to increase epidermal aeration. One manufacturer of tape products with these qualities is the 3M Company. The tape can come precut into one half inch by two inches strips with paper tabs to facilitate easy application. The paper backing is removed and the tape is placed on the rectangular section of each wing on the rear surface. The second paper backing of the tape may then be removed to allow the undergarment to adhere to the skin. When the pad assembly is removed for washing, the tape is taken off and new tape strips are applied prior to reuse. No chemicals are necessary in the application of this undergarment to the skin that could interfere with breastfeeding or wound healing.

Note that dimensions and design are for example only and different sizes and embroideries can be used to customize the design to particular applications and individuals (e.g. wound vs. breast application; wound or breast size variation).

Included in this invention is a method for absorbing fluid from a nipple or a surgical wound and enabling the nipple or surgical wound to be repeatedly exposed for nursing, examination, or treatment without removal of the pad assembly. The method involves attaching a pad assembly, having a pocket capable of receiving an absorbent padding material as previously described, to an area surrounding the nipple or surgical wound in such a fashion that the padding material will contact the nipple or surgical wound through the rear opening. In addition, the padding material may be removed through the front opening to expose the nipple or surgical wound for the purpose of nursing, examination, or treatment thereof.

I claim:

1. A shoulder-strapless nursing pad assembly suitable for absorbing lacteal fluid, said pad assembly comprising:

a conformable casing having a front, a rear, a central area and a plurality of outwardly extending fingers, said central area including a pocket having an absorbent padding material located therein, said pocket further having a rear opening, and a front opening including no external flaps, tabs or cover strips to retain the absorbent padding material, said extending fingers each having a proximal end and distal end;

the absorbent padding material located in said pocket capable of being removed through said front opening;

means for attaching said outwardly extending fingers to an area surrounding a nipple in such a fashion that the nipple will contact said absorbent padding material through said rear opening; and slits on opposite sides of the opening, one hundred eighty degrees separated from one another, in the front of the casing for allowing easy insertion of the absorbent padding material and increased access to the nipple for nursing;

whereby when said absorbent padding material is removed from said pocket, the nipple will be exposed through said front opening to enable nursing, without requiring removal of the entire pad assembly, and without inhibition from external flaps, tabs or cover strips on said front opening.

2. The pad assembly of claim 1, wherein said plurality of outwardly extending fingers comprises a plurality of strips spaced symmetrically about said central area.

3. The pad assembly of claim 1, wherein said plurality of outwardly extending fingers have generally decreasing width as a function of distance from said central area.

4. The pad assembly of claim 1, wherein said plurality of outwardly extending fingers have generally decreasing width as a function of distance from said central area followed by increasing width at the distal end so as to form the shape of a formee cross to enhance contouring to a breast and to improve adhesive capabilities.

5. The pad assembly of claim 1, wherein said conformable casing comprises a flexible fabric.

6. The pad assembly of claim 1, wherein said conformable casing comprises a polyurethane elastomer.

7. The pad assembly of claim 1, where said conformable casing is formed from front and rear pieces of flexible fabric secured together forming between them a pocket to receive the absorbent padding material.

8. A pad assembly of claim 1, where the front and rear openings in the comformable casing are centrally located.

9. A pad assembly in claim 1, where the front opening of the casing is smaller than the rear opening to prevent the absorbent padding material from dislodging.

10. A pad assembly in claim 1, where the rear opening of the casing is smaller than the front opening to facilitate nursing an infant.

11. A pad assembly in claim 1, where edges of said pad assembly are oversewn to prevent material fraying.

12. A pad assembly of claim 1, where the absorbent padding material is washable and reusable.

13. A pad assembly of claim 1, where the said means for attaching comprises double-sided adhesive tape strips.

14. A pad assembly of claim 13, where the adhesive tape strips are removably attached so that new tape strips can be attached in place of said adhesive tape strips.

15. A pad assembly of claim 13, wherein said means for attaching are hypoallergenic, microporous, double-sided, adhesive tape strips.

16. A method for absorbing lacteal fluid from a nipple and enabling said nipple to be repeatedly exposed for nursing comprising the steps of:

providing a shoulder strapless nursing pad assembly suitable for absorbing lacteal fluid, said pad assembly comprising:

a conformable casing having a front, a rear, a central area and a plurality of outwardly extending fingers, said central area including a pocket having an absorbent padding material located therein, said pocket further having a rear opening, and a front opening including no external flaps, tabs or cover strips to retain the absorbent padding material, said extending fingers each having a proximal end and distal end;

the absorbent padding material located in said pocket capable of being removed through said front opening;

means for attaching said outwardly extending fingers to an area surrounding a nipple in such a fashion that the nipple will contact said absorbent padding material through said rear opening; and slits on opposite sides of the opening, one hundred eighty degrees separated from one another, in the front of the casing for allowing easy insertion of the absorbent padding material and increased access to the nipple for nursing;

whereby when said absorbent padding material is removed from said pocket, the nipple will be exposed through said front opening to enable nursing, without requiring removal of the entire pad assembly, and without inhibition from external flaps, tabs or cover strips on said front opening; and attaching said shoulder-strapless nursing pad assembly to said area surrounding said nipple with said attaching means in said fashion such that the nipple that contacts said absorbent padding material through said rear opening;

whereby said absorbent padding material of said pad assembly will absorb said fluid from said nipple.

* * * * *